United States Patent [19]

Wiegers et al.

[11] Patent Number: 4,666,629

[45] Date of Patent: * May 19, 1987

[54] PROCESS FOR PREPARING MIXTURE CONTAINING 2-CAMPHOLENYLIDENBUTANOL, PRODUCT PRODUCED THEREBY AND PERFUMERY USES THEREOF

[75] Inventors: Wilhelmus J. Wiegers, Red Bank; Mark A. Sprecker, Sea Bright; William L. Schreiber, Jackson, all of N.J.

[73] Assignee: International Flavors & Fragrances Inc., New York, N.Y.

[*] Notice: The portion of the term of this patent subsequent to Oct. 28, 2003 has been disclaimed.

[21] Appl. No.: 894,964

[22] Filed: Aug. 8, 1986

Related U.S. Application Data

[62] Division of Ser. No. 778,442, Sep. 20, 1985, Pat. No. 4,619,781.

[51] Int. Cl.⁴ .......................... C11B 9/00; A61K 7/46
[52] U.S. Cl. ................................ 252/522 R; 568/838
[58] Field of Search ..................... 568/838; 252/522 R

[56] References Cited

U.S. PATENT DOCUMENTS 4,052,341 10/1977 Naipawer et al. ................. 252/522
4,210,767 7/1980 Yoshida et al. .................... 568/345

FOREIGN PATENT DOCUMENTS 68936 9/1969 Fed. Rep. of Germany ... 252/522 R
1922391 8/1970 Fed. Rep. of Germany ... 252/522 R

OTHER PUBLICATIONS

Tokai Tokkyo Yoho, "Chemical Abstracts", vol. 94 (1981) 120971e.
"Harshaw Catalysts", pp. 8-9 and front cover, published by Harshaw Chem. Co., 23800 Mercantile Road, Beachwood, Ohio 44122.
"Catalysts from Calsicat", p. on Copper Chromite Catalysts and front cover, published by Calsicat Div. of Mallinckrodt, Inc., Erie, Pa. 16503-2497.

Primary Examiner—Werren B. Lone
Attorney, Agent, or Firm—Arthur L. Liberman

[57] ABSTRACT

Described is an economical and novel process for preparing a mixture containing 2-campholenylidenbutanol having the structure:

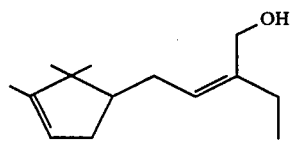

by means of reacting the compound having the structure:

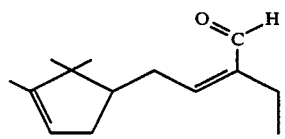

with hydrogen in the presence of a copper chromite catalyst having the formula:

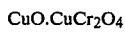

$CuO \cdot CuCr_2O_4$ as well as uses of such mixtures in augmenting or enhancing the aroma of perfume compositions, colognes and perfumed articles including fabric softener compositions, cosmetic powders and solid or liquid anionic, cationic, nonionic or zwitterionic detergents.

5 Claims, 9 Drawing Figures

GLC PROFILE FOR EXAMPLE I, CRUDE 9 HOURS.

GLC PROFILE FOR EXAMPLE I, CRUDE 9 HOURS.

GLC PROFILE FOR BULKED FRACTIONS 12-16 OF EXAMPLE I.

GLC PROFILE FOR EXAMPLE I, CRUDE (30 HOURS)

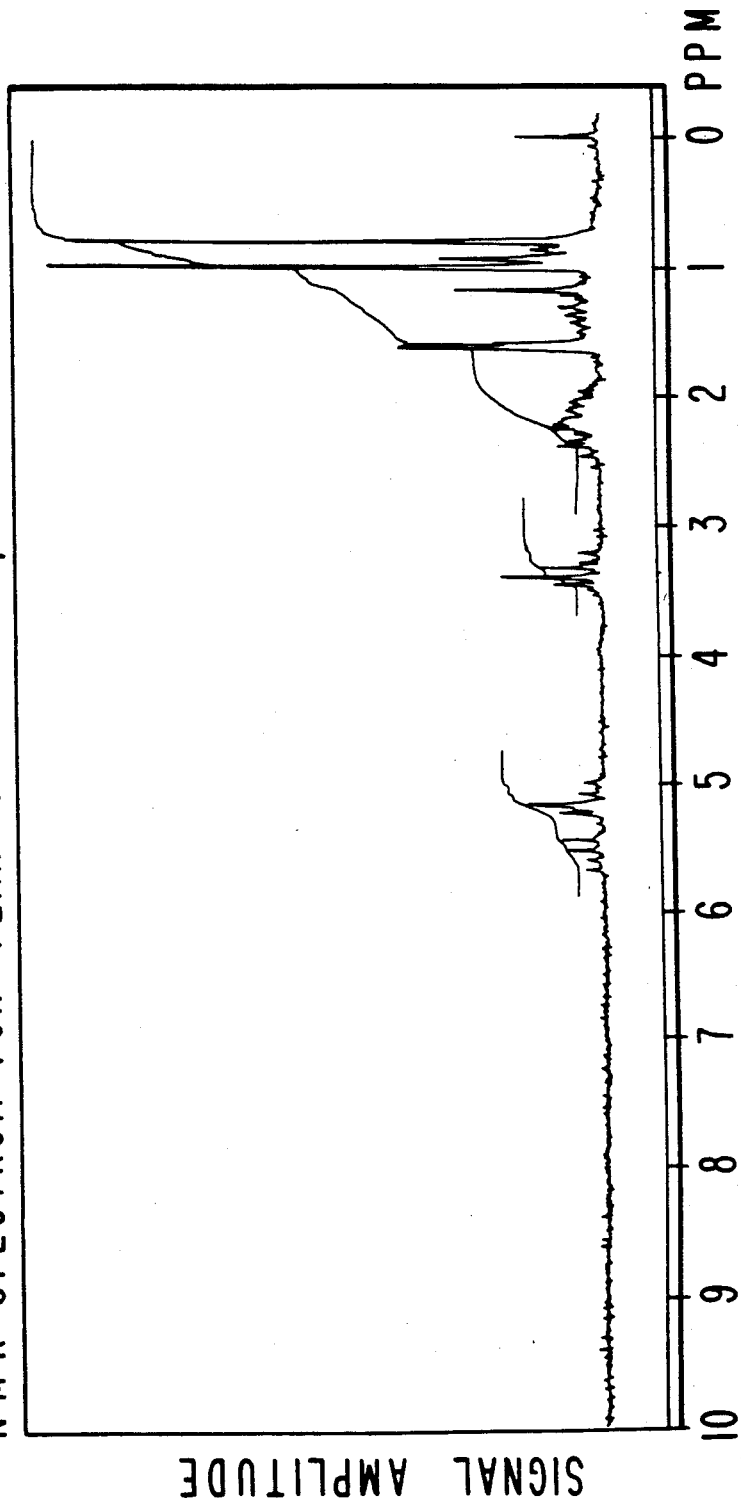

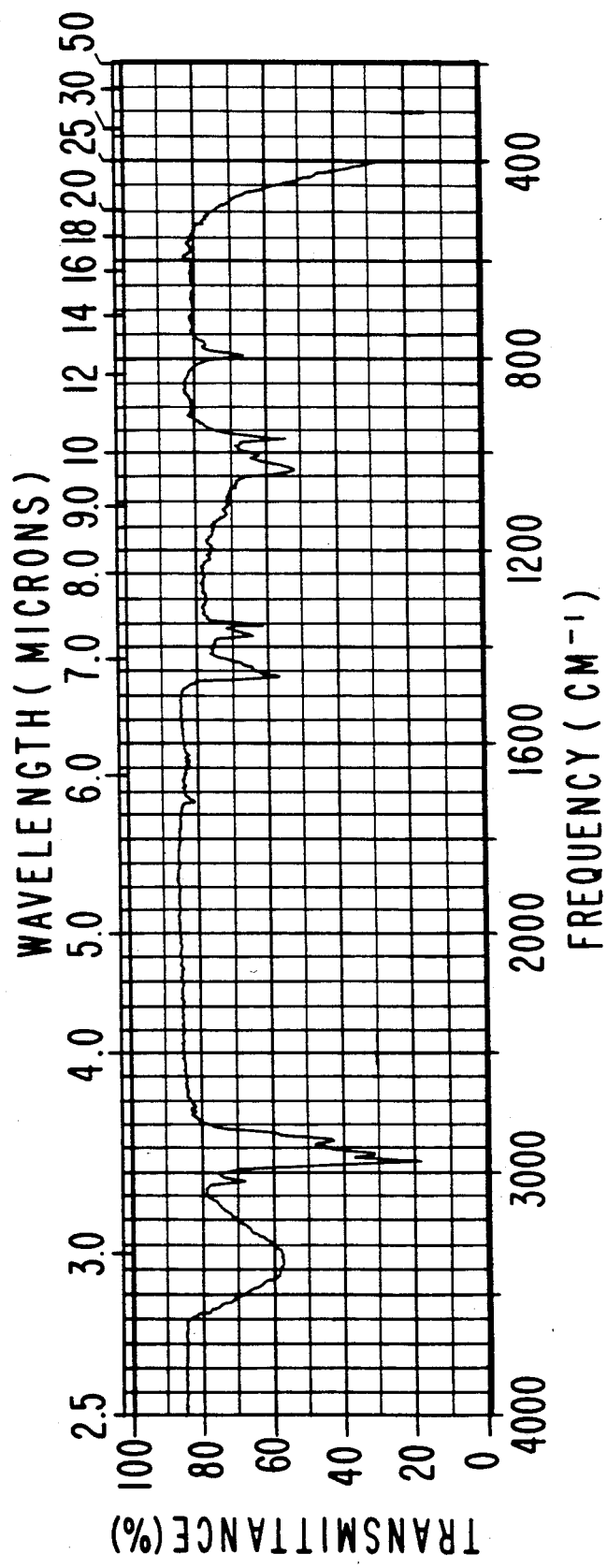

NMR SPECTRUM FOR PEAK 13 OF FIG. 1, EXAMPLE I.

NMR SPECTRUM FOR PEAK 14 OF FIG.1, EXAMPLE I

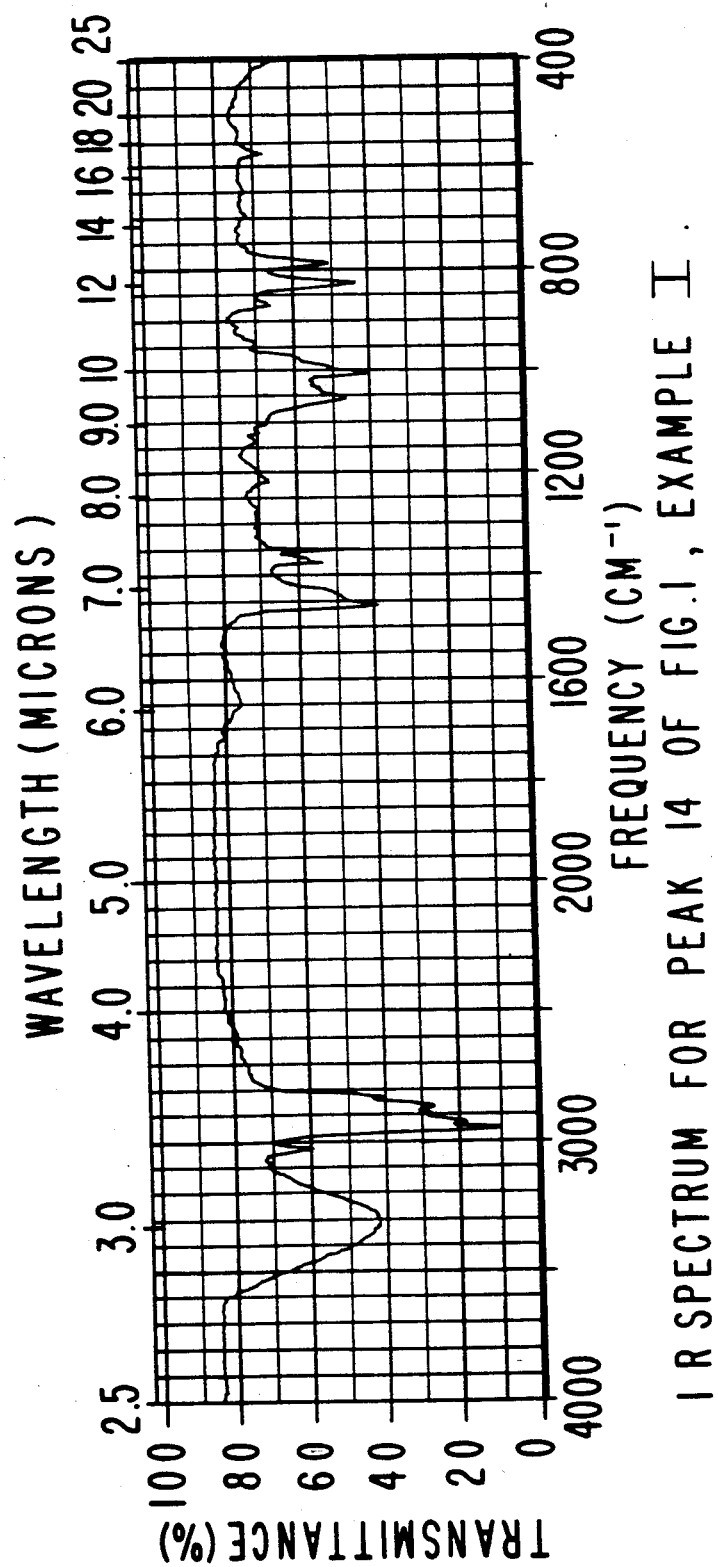

PROCESS FOR PREPARING MIXTURE CONTAINING 2-CAMPHOLENYLIDENBUTANOL, PRODUCT PRODUCED THEREBY AND PERFUMERY USES THEREOF

This is a divisional of application Ser. No. 778,442, filed on Sept. 20, 1985, now U.S. Pat. No. 4,619,781.

BACKGROUND OF THE INVENTION

Our invention describes a novel, economical process for preparing 2-campholenylidenbutanol by means of reacting the compound having the structure:

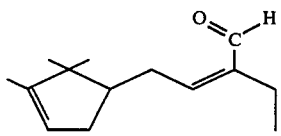

with hydrogen in the presence of a copper chromite catalyst over a specific range of reaction conditions.

There is a continuing search for materials having desirable fragrance properties. Such materials are used either to replace costly natural materials or to provide new fragrances of perfumed types which have not heretofore been available. Especially desirable qualities for substances having interesting fragrances such as sandalwood-type fragrances are stability and persistence, particularly in a wide variety of perfumed articles (e.g., soaps, detergents and powders), perfumed compositions and colognes, ease of manufacture and intensity of aroma.

Furthermore, according to Guenther [E. Guenther, "The Essential Oils", Vol. V. page 173, D. Van Nostrand Co., New York (1952)], East Indian sandalwood oil "has been perhaps one of the most precious perfumery materials from antiquity down to modern times, and its popularity has shown no signs of waning." This oil is widely used in perfumery, and would be even more widely used except for its limited supply and high cost.

As is well known, a need exists for synthetic substances which can be used as sandalwood substitutes or extenders. It would be most desirable to be able to synthetically provide the major odorant compound of the natural sandalwood oil, i.e., alpha-santalol and beta-santalol, but no commercially feasible route to these chemicals is known at this time.

It would be even more desirable to provide a synthetic compound which would have many of the desirable odor qualities of a fine East Indian sandalwood oil, yet not have the potentially labile primary allylic alcohol group present in the natural santalols. A compound which would be more resistant to acidic or oxidative decomposition as well as being base stable could be even more versatile than sandalwood oil itself.

There is no obvious explanation why only slight chemical changes should have such a dramatic effect on odor intensity other than to invoke the general unreliability of odor structure relationships. Why the addition or removal of a methyl group, the removal of a double bond or the mere moving of a methyl group would essentially destroy more than 90% of the odor intensity rather than merely cause subtle odor differences comparable to the subtle chemical differences cannot be explained by any theoretical concepts in the known art.

U.S. Pat. No. 4,052,341 issued on Oct. 4, 1977 provides a sandalwood type aroma imparting material having one of the structures:

TABLE I

| NAME | STRUCTURE |
| --- | --- |
| 3-Methyl-5-(2,2,3-trimethylcyclopent-3-en-1-yl)pentan-2-ol | 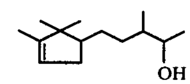 |
| 3-Methyl-5-(2,2,3-trimethylcyclopentan-1-yl)pentan-2-ol | 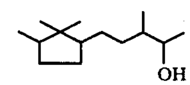 |
| 5-(2,2,3-Trimethylcyclopent-3-en-1-yl)pentan-2-ol | |
| 6-(2,2,3-Trimethylcyclopent-3-en-1-yl)hexan-3-ol | |
| 4-Methyl-6-(2,2,3-trimethylcyclopent-3-en-1-yl)hexan-3-ol | 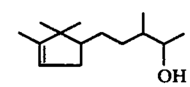 |
| 3-Ethyl-5-(2,2,3-trimethylcyclopent-3-en-1-yl)pentan-2-ol | 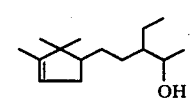 |
| 3-Methyl-5-(2,3,3-trimethylcyclopent-3-en-1-(R)—yl)pentan-2-ol | 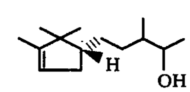 |
| 3-Methyl-5-(2,2,3-trimethylcyclopent-3-en-1-(S)—yl)pentan-2-ol | 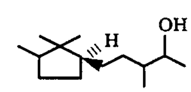 |
| 3-Methyl-5-(2,2,3-trimethylcyclopent-3-en-1-yl)pent-3-en-2-ol | 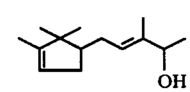 |

These materials are produced according to the reaction schemes:

TABLE II

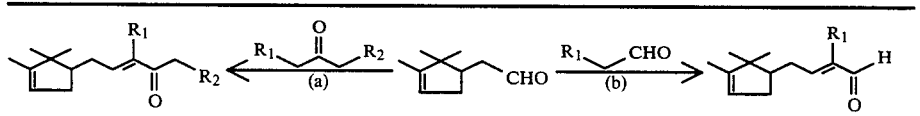

TABLE II-continued

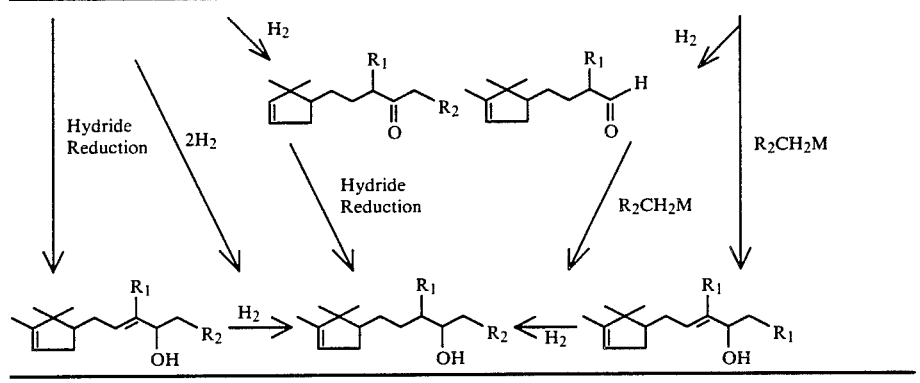

(a) $R_1$ = H, $CH_3$, $C_2H_5$
$R_2$ = H, $CH_3$

East German Pat. No. 68,936 discloses for use in the sandalwood area a compound having the structure:

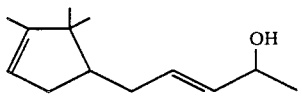

Furthermore, Chemical Abstracts Volume 72, 125008b sets forth a genus for the East German Pat. No. 68,936 encompassing the following group of compounds:

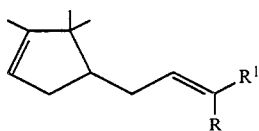

wherein R=$CH_2OH$, $CHCH_3OH$ and $R^1$=H, $CH_3$ or $C_2H_5$.

Furthermore, U.S. Pat. No. 4,210,767 issued on July 1, 1980 discloses the process for preparing aldehydes and ketones according to the reaction scheme:

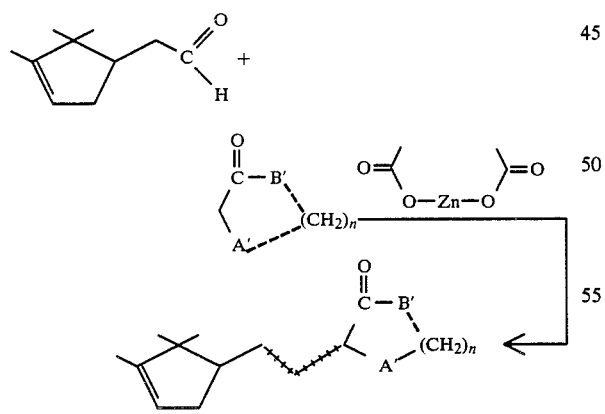

wherein x is 0 or 2; wherein one of the lines + + + + + + is a carbon-carbon double bond and the other of the lines + + + + + + is a carbon-carbon single bond; wherein A' is one of hydrogen, $C_3C_2H_5$ or —$CH_2$— and B' is hydrogen, $CH_3$, $C_2H_5$ or —$CH_2$—; n is 0, 1 or 2; each of the dashed lines represents a carbon-carbon single or no bond; with the proviso that A' and B' is both —$CH_2$— when n=1 or n=2 and the dashed line represents a carbon-carbon single bond; and A' is hydrogen and B' is $C_2H_5$ or $CH_3$ or A' is $CH_3$ and B' is $CH_3$ or $C_2H_5$ and n is 0 and the dashed line represents no bond comprising the steps of intimately admixing campholenic aldehyde with a ketone having the structure:

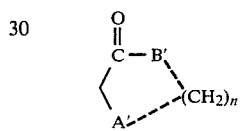

in the presence of a catalyst selected from the group consisting of zinc acetate and zinc acetate dihydrate; said reaction being carried out in the liquid phase at an elevated temperature sufficient to produce the desired product.

U.S. Pat. No. 4,210,767 further describes the process step according to the additional reaction scheme:

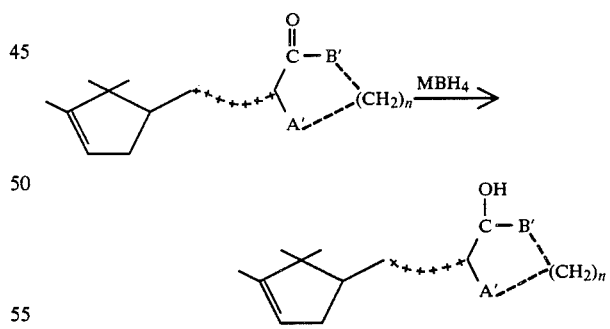

wherein M is alkali metal selected from the group consisting of potassium and sodium, comprising the steps of admixing an alkaline metal borohydride with the ketone reaction product having the structure:

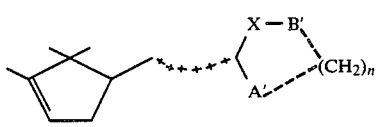

wherein X has the structure:

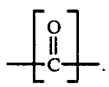

Nothing in the prior art shows such a process, however, utilizing a copper chromite catalyst whereby a novel reaction product is produced.

Copper chromite catalysts of the formula:

$$CuO \cdot CuCr_2O_4$$

are described in the catalogues by their manufacturers, to wit:

(i) Harshaw Chemical Co. of Beachwood, Ohio 44122, entitled "Harshaw Catalysts" and
(ii) Calsicat Division of Mallinchkrodt, Inc. of Irie, Pa. 16503-2497, entitled "Catalysts From Calsicat".

At page 8 of the Harshaw catalogue it is stated:

"Copper chromite catalysts find application where reduction of functional groups are desired while maintaining the unsaturation of aromatic rings or alkyl chains."

The Calsicat "Catalysts" catalogue states, inter alia:

"Copper Chromite Catalysts . . . Applications include the hydrogenation of aldehydes . . . "

Nothing set forth in the commercial literature pertaining to the copper chromite catalysts suggests the use of the copper chromite catalyst in the reduction reaction:

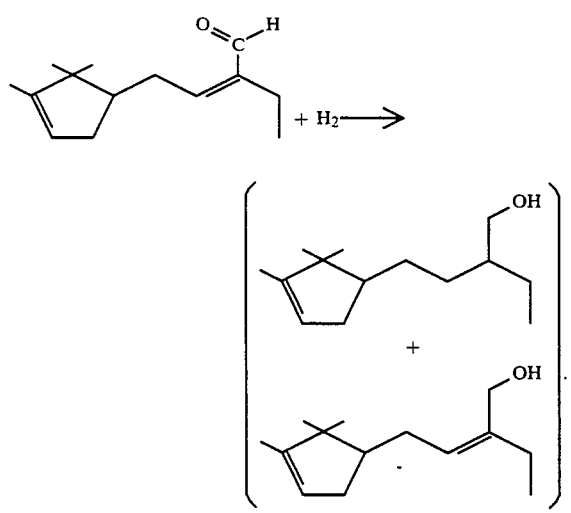

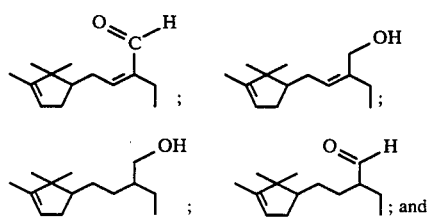

(Conditions: 10'×0.25" 10% carbowax column programmed at 150°–225° C. at 8° C. per minute).

Figure 2:
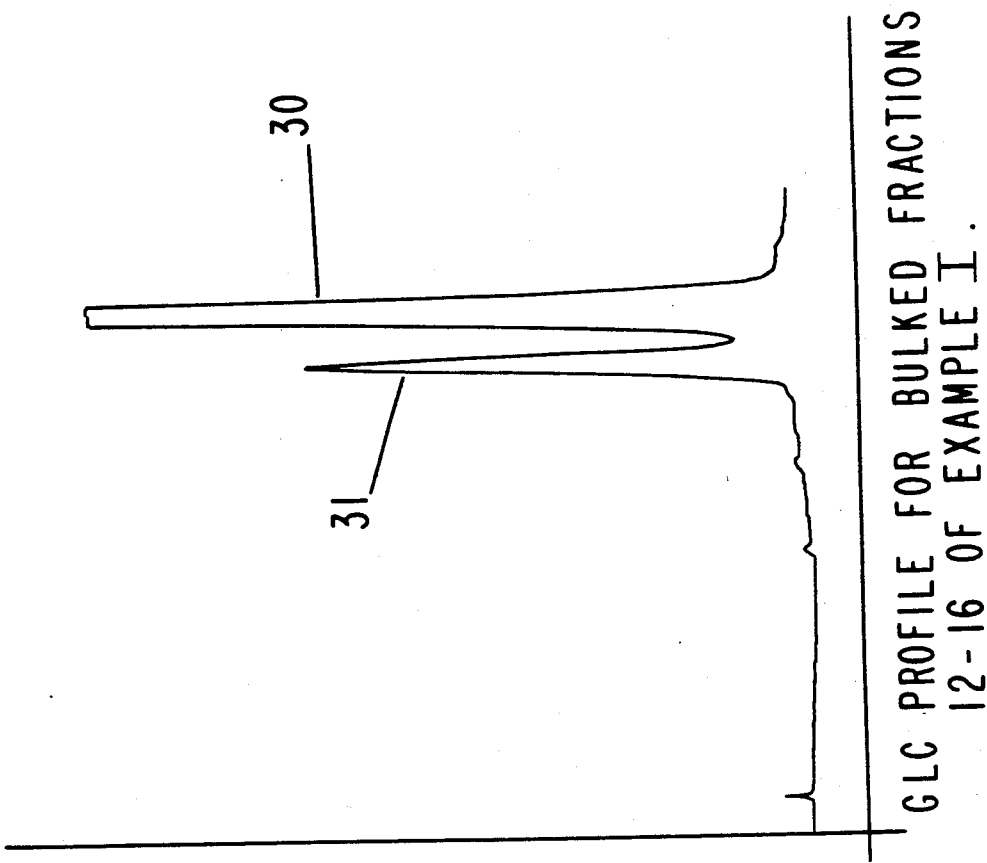

FIG. 2 is the GLC profile for the crude reaction product of Example I after 30 hours of reaction whereat the reaction product contains the compounds having the structures:

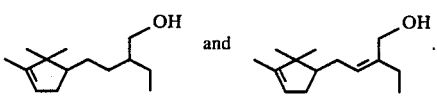

Figure 3:
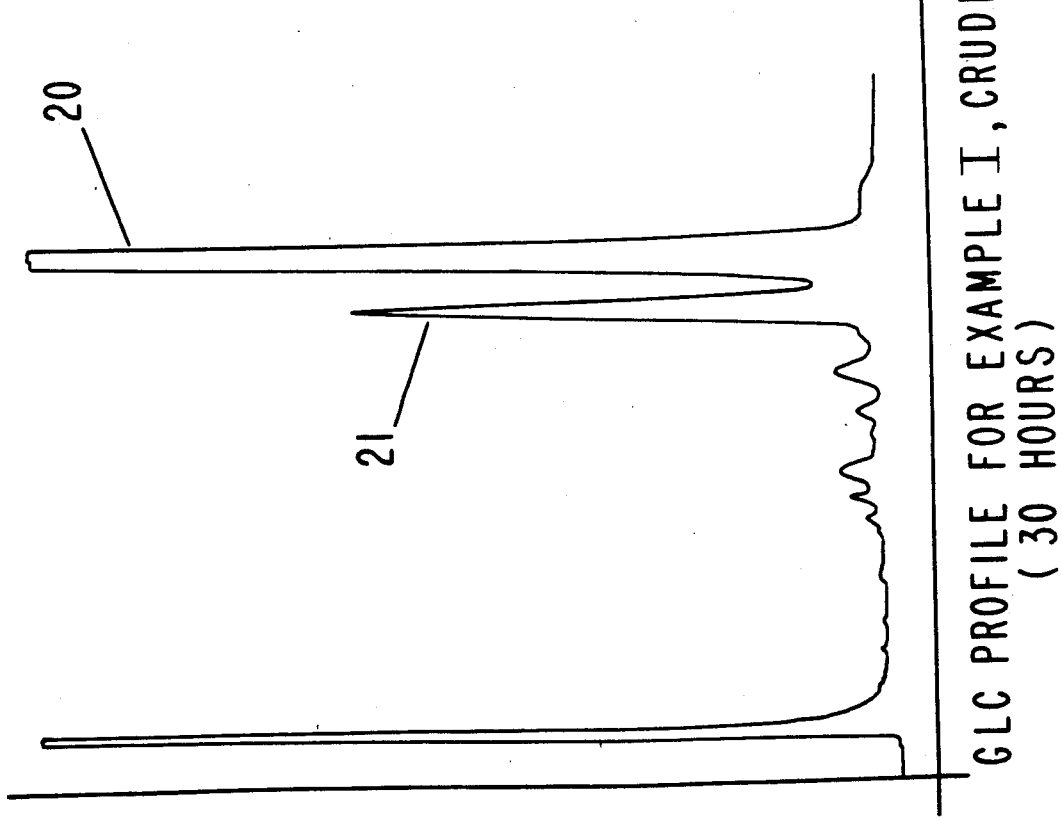

FIG. 3 is the GLC profile for the bulked distillation fractions 12–16 of the distillation of the reaction product of Example I containing the compounds having the structures:

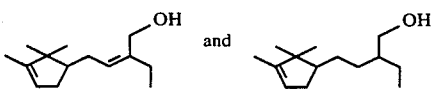

(Conditions: 10'×0.25" 10% carbowax column programmed at 150°–225° C. at 8° C. per minute).

Figure 1:
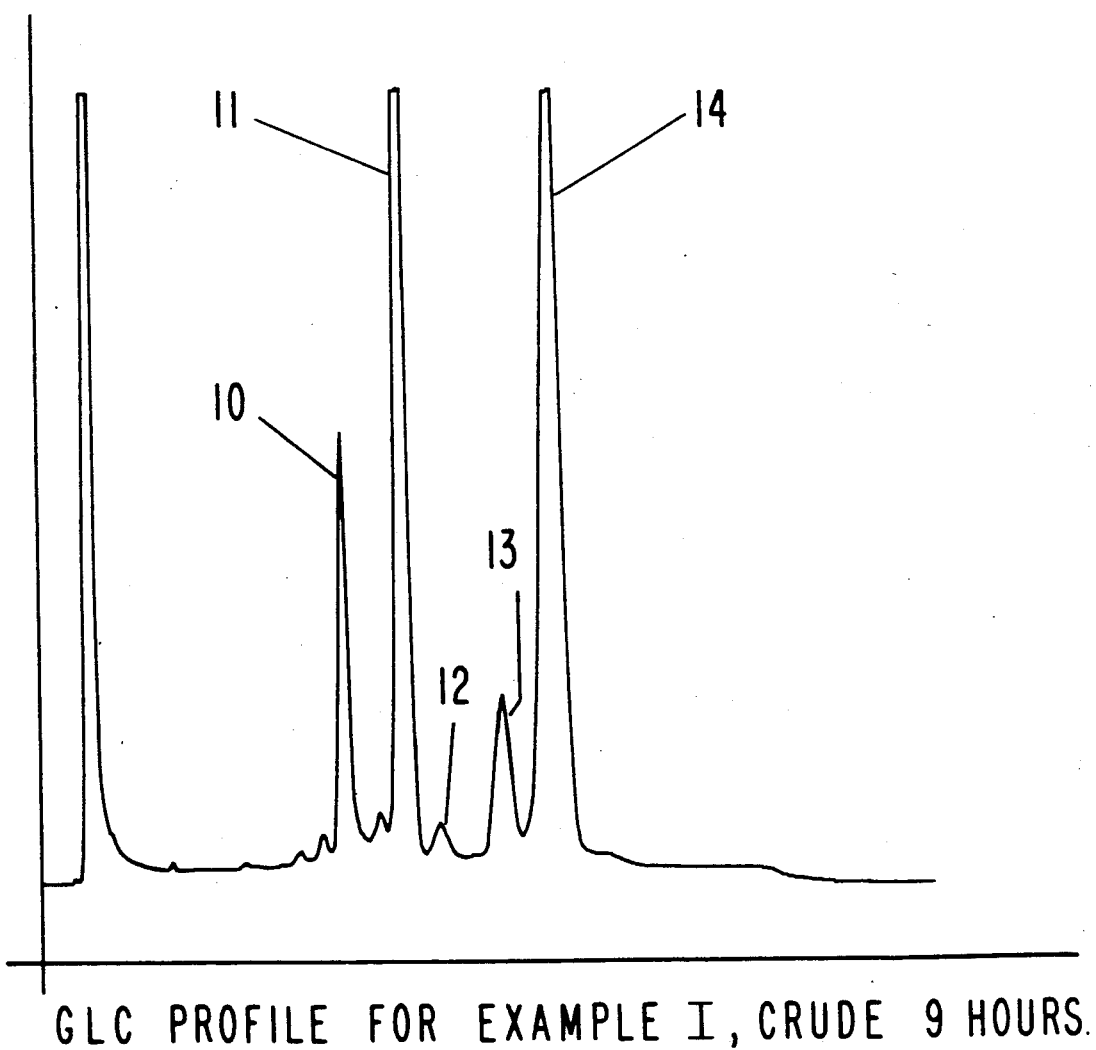
FIG. 1 is the GLC profile for the crude reaction product of Example I after nine hours of reaction wherein the reaction products having the structures.

FIG. 4 is the NMR spectrum for the peak indicated by reference numeral 12 on the GLC profile of FIG. 1 which is for the compound having the structure:

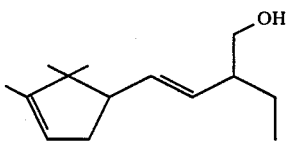

(Conditions: Field strength: 100 MHz; solvent: CFCl₃).

FIG. 5 is the infra-red spectrum for the compound of the peak indicated by reference numeral 12 in the GLC profile of FIG. 1, said compound having the structure:

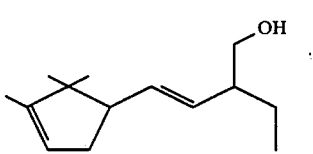

Figure 6:
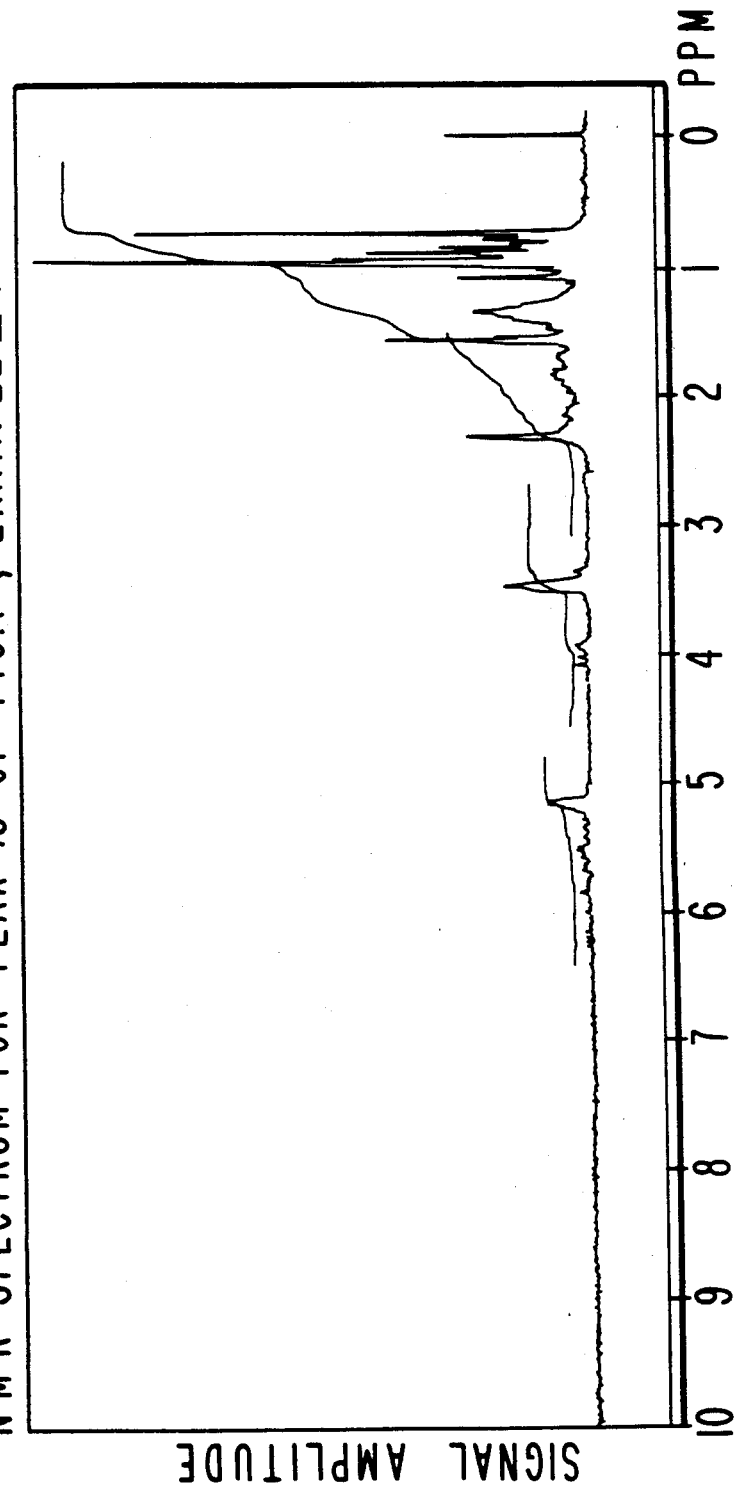

FIG. 6 is the NMR spectrum for the peak indicated by reference numeral 13 of the GLC profile of FIG. 1, for the compound having the structure:

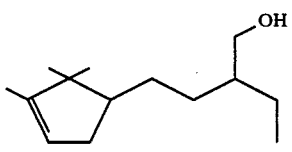

(Conditions: Field strength: 100 MHz; solvent: CFCl₃).

Figure 7:
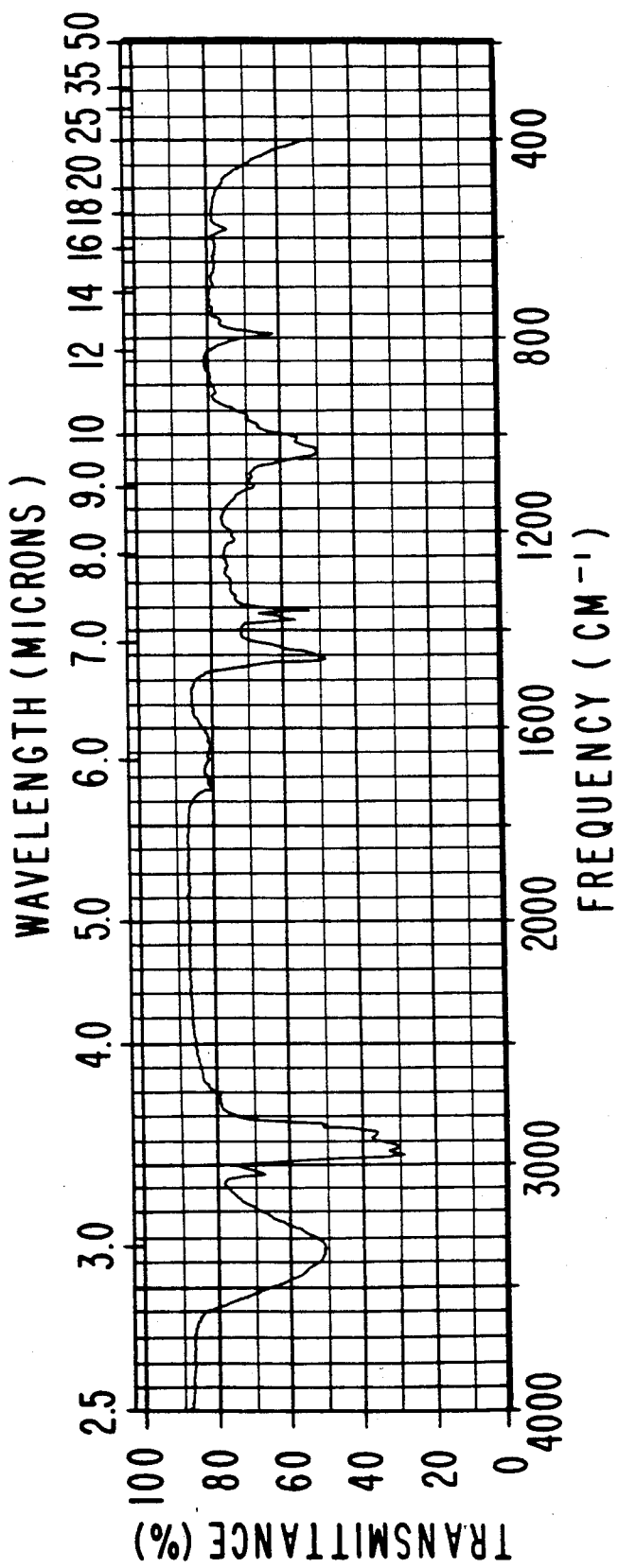

FIG. 7 is the infra-red spectrum for the peak indicated by reference numeral 13 of the GLC profile of FIG. 1 for the compound having the structure:

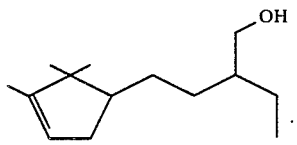

Figure 8:
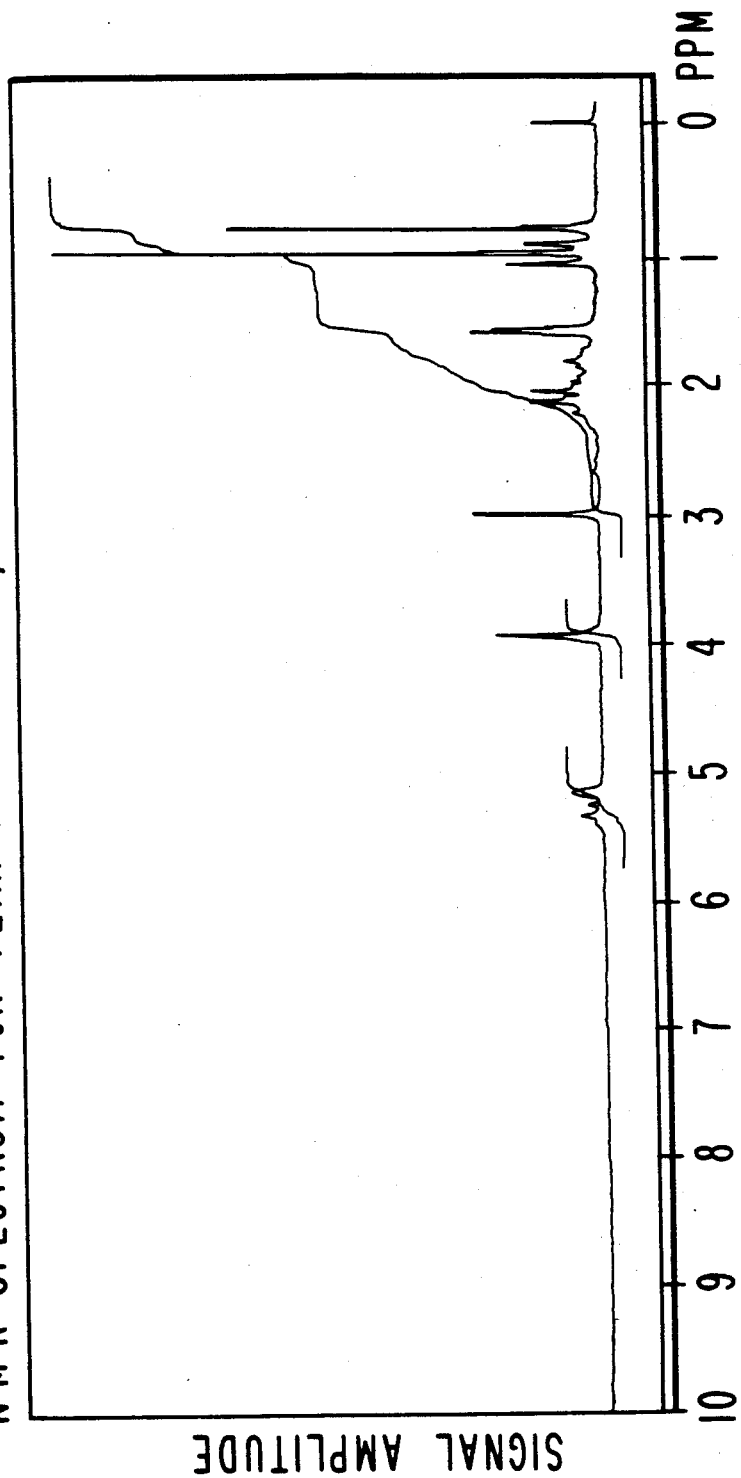

FIG. 8 is the NMR spectrum for the peak indicated by reference numeral 14 of the GLC profile of FIG. 1 for the compound having the structure:

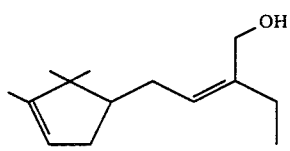

(Conditions: Field strength: 100 MHz; solvent: CFCl$_3$).

FIG. 9 is the infra-red spectrum for the peak indicated by reference numeral 14 of the GLC profile of FIG. 1 for the compound having the structure:

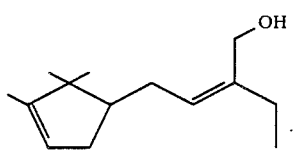

DETAILED DESCRIPTION OF THE DRAWINGS

FIG. 1 is the GLC profile for the crude reaction product of Example I after nine hours of reaction. (Conditions: 10'×0.25" 10% carbowax column programmed at 150°–225° C. at 8° C. per minute).

The peak indicated by reference numeral 10 is the peak for the compound having the structure:

The peak indicated by reference numeral 11 is the peak for the compound having the strucure:

The peak indicated by reference numeral 12 is the peak for the compound having the structure:

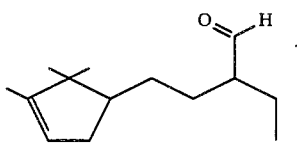

The peak indicated by reference numeral 13 is the peak for the compound having the structure:

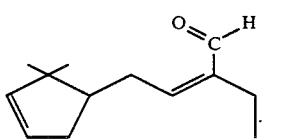

The peak indicated by reference numeral 14 is the peak for the compound having the structure:

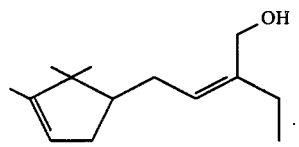

FIG. 2 is the GLC profile for the crude reaction product of Example I after 30 hours of reaction.

The peak indicated by reference numeral 20 is the peak for the compound having the structure:

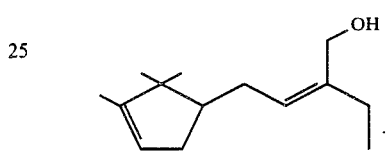

The peak indicated by reference numeral 21 is the peak for the compound having the structure:

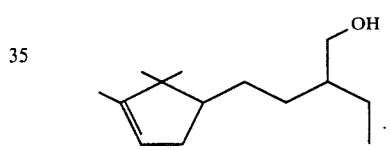

FIG. 3 is the GLC profile for bulked distillation fractions 12–16 of the distillation of the reaction product of Example I.

The peak indicated by reference numeral 30 is the peak for the compound having the structure:

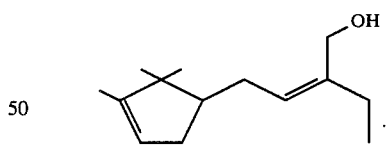

The peak indicated by reference numeral 31 is the peak for the compound having the structure:

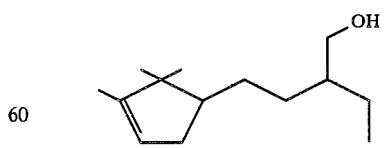

(Conditions: 10'×0.25" 10% carbowax column programmed at 150°–225° C. at 8° C. per minute).

THE INVENTION

Our invention covers a novel and economically viable process for producing a novel perfume mixture containing proportion of the valuable sandalwood compound having the structure:

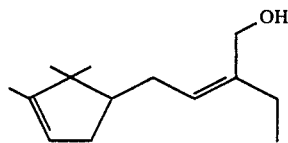

and a minor proportion of the compound having the structure:

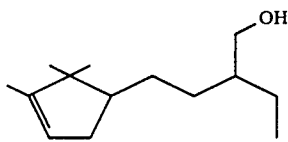

by means of hydrogenating the aldehyde having the structure:

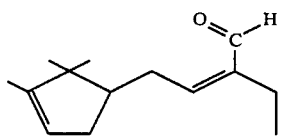

in the presence of a copper chromite catalyst having the formula:

The starting material which is the aldehyde having the structure:

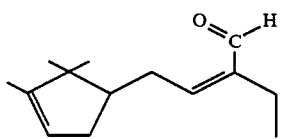

is prepared by means of an aldol condensation reaction, to wit:

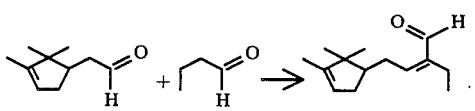

Such aldol condensations are well known to those having ordinary skill in the art and are described in detail in U.S. Pat. No. 4,210,767 issued on July 1, 1980 the specification for which is incorporated by reference herein. Such aldol condensations are further described in the East German Pat. No. 68,936 published on May 8, 1968 (the specification for which is incorporated by reference herein) and the West German Offenlegungsschrift No. 1,922,391 published on Aug. 27, 1970 (the specification for which is incorporated by reference herein). The reaction products of our invention have intense, long-lasting and aesthetically pleasing woody and sandalwood aromas causing them to be useful in formulating perfume compositions, perfumed articles and colognes.

The reaction of our invention, to wit:

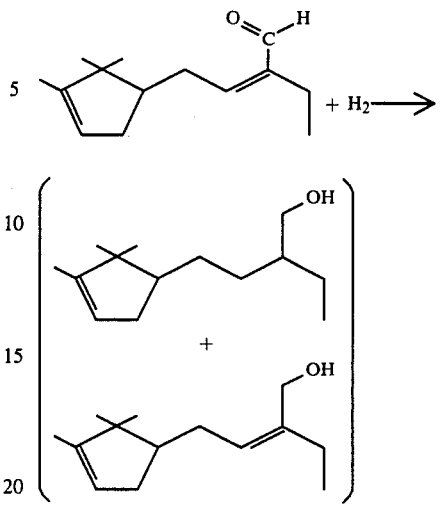

proceeds in such a way that during the reaction certain additional intermediates are produced, to wit:
(i) The compound having the structure:

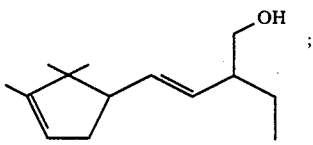

and
(ii) the compound having the structure:

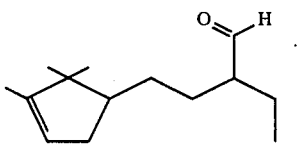

At the end of the reaction the reaction mass primarily consists of compounds having the structures:

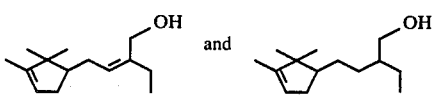

with a predominance of the compound having the structure:

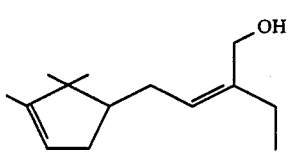

and a number of other unidentified compounds as will be seen by a perusal of the GLC profile for Example I, infra.

The copper chromite catalyst for the reaction having the formula:

may be, for example:

| HARSHAW CATALYSTS: | | |
|---|---|---|
| Cu 1129 P: | | |
| Average Bulked Density | 47 | lbs. per cubic foot |
| Surface Area | 25 | m² per gram |
| CuO | 43% | |
| Cr₂O₃ | 45% | |
| BaO | 8% | |
| Cu 1920 P: | | |
| Average Bulked Density | 37 | lbs. per cubic foot |
| Surface Area | 56 | m² per gram |
| CuO | 46% | |
| Cr₂O₃ | 46% | |
| MnO | 4.0% | |
| Cu 1800 P: | | |
| Average Bulked Density | 41 | lbs. per cubic foot |
| Surface Area | 30 | m² per gram |
| CuO | 51% | |
| Cr₂O₃ | 46% | |
| Cu 1803 P: | | |
| Average Bulked Density | 20 | lbs. per cubic foot |
| Surface Area | 46 | m² per cubic foot |
| CuO | 52% | |
| Cr₂O₃ | 46% | |
| CALSICAT CATALYSTS: | | |
| E-108 P: | | |
| Average particle size | 10 | microns |
| Surface area, m² per gram | 80 | |
| Contains BaO | | |
| E-105 P: | | |
| Average particle size | 10 | microns |
| Surface area m² per gram | 50 | |

Prior to carrying out the reaction the copper chromite catalyst is activated by heating the catalyst at high pressures, e.g., 200 psig–500 psig at a temperature of between about 110° and 140° C. for a period of time of between about one hour and about four hours.

The hydrogenation reaction, to wit:

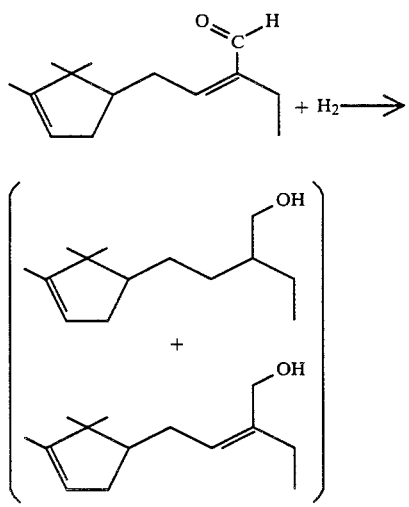

takes place at a temperature in the range of from about 110° C. up to about 220° C. at pressures of between about 100 psig and about 1000 psig for a period of time of between about 10 hours up to about 40 hours.

The weight percent of copper chromite catalyst in the reaction mass based on aldehyde having the structure:

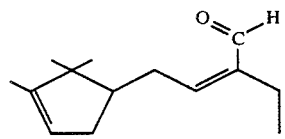

is from about 1 weight percent up to about 6 weight percent.

The reaction is preferably terminated when a majority of the reaction product (e.g., 70–80%) is a compound having the structure:

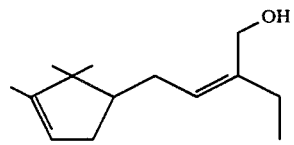

and the remainder of the reaction mass is primarily the compound having the structure:

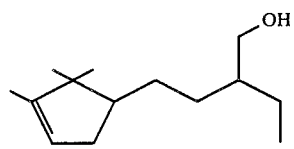

with other reaction products being present in very minor proportions.

About halfway through the reaction relatively large proportions of other side products exist in the reaction mass, for example, the starting material having the structure:

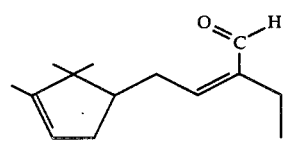

and the compounds having the structures:

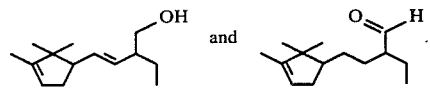

Depending upon the desired perfumery uses (e.g., quality, substantivity and strength of sandalwood aroma) the reaction may be terminated at any point in time desired for a specific utility in perfumery. Optimally, the reaction is stopped when between about 70 and about 80% of the compound having the structure:

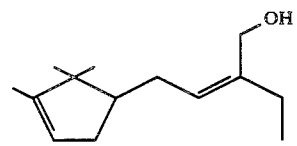

is formed. That does not necessarily mean that for a specific perfume use the reaction may not be stopped at an earlier point in time whereby larger quantities of compound having the structure:

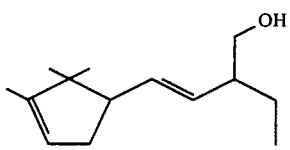

are formed. If the reaction is run too long (e.g., upwards of 50–60 hours) an excess of quantity of the compound having the structure:

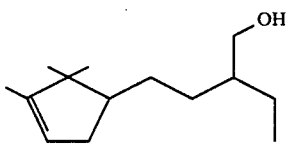

is formed which is not desirable from a perfumery standpoint.

Thus, in the following paragraphs, the term "mixture of compounds containing 2-campholenylidenbutanol" refers to the mixture of compounds, to wit:

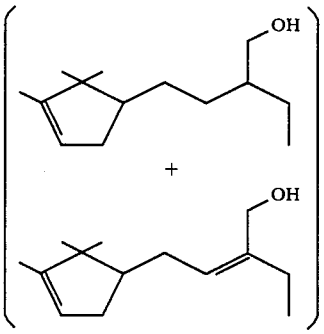

with between 70 and 80% of this mixture being the compound having the structure:

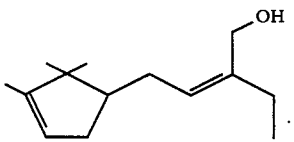

At the end of the reaction the reaction mass is fractionally distilled and appropriate distillation fractions are taken for various uses in perfumery, that is in augmenting or enhancing the aroma of perfume compositions, colognes and perfumed articles, e.g., solid or liquid anionic, cationic, nonionic or zwitterionic detergents, hair preparations, cosmetic powders, fabric softener compositions and fabric softener articles (e.g., dryer-added fabric softener articles). In addition, the reaction products of our invention have utility as malodor maskants, e.g., in masking urine and fecal aromas.

The mixture containing 2-campholenylidenbutanol of our invention can be incorporated into a wide variety of compositions each of which will be enhanced or augmented by its rich sandalwood and woody aroma nuances. The mixture containing 2-campholenylidenbutanol of our invention can be added to perfume compositions per se or it can be added in admixture with other fragrance materials in order to provide a desired fragrance character to a finished perfumed material.

The perfume and fragrance compositions obtained according to our invention are suitable in a wide variety of perfumed articles and can also be used to enhance, modify or reinforce natural fragrance materials. It will thus be appreciated that the mixture containing 2-campholenylidenbutanol of our invention is useful as an olfactory agent in fragrance.

The term "perfume composition" is used herein to mean a mixture of compounds including, for example, natural oils, synthetic oils, alcohols other than those covered by the alcohols produced according to this invention, aldehydes, ketones, esters, lactones, nitriles and frequently hydrocarbons which are admixed so that the combined odors of the individual components produce a pleasant or desired fragrance. Such perfume compositions usually contain (a) the main note or the "bouquet" or foundation stone of the composition; (b) modifiers which round-off and accompany the main note; (c) fixatives which include odorous substances which lend a particular note to the perfume throughout all stages of evaporation, and substances which retard evaporation; and (d) topnotes which are usually low-boiling fresh-smelling materials. Such perfume compositions of our invention can be used in conjunction with carriers, vehicles, solvents, dispersants, emulsifiers, surface-active agents, aerosol propellants and the like.

In perfume compositions the individual components contribute their particular olfactory characteristics, but the overall effect of the perfume composition will be the sum of the effect of each ingredient. Thus, the mixture containing 2-campholenylidenbutanol of our invention can be used to alter, augment, modify or enhance the aroma characteristics of a perfume composition or perfumed article for example by highlighting or moderating the olfactory reaction contributed by another ingredient of the composition.

The amount of the mixture containing 2-campholenylidenbutanol of our invention which will be effective in perfume compositions depends upon many factors including the other ingredients, their amounts and the effects which are desired. It has been found that perfume compositions containing as much as much as 70% or as little as 0.1 ppm (0.00001%) by weight of the mixture containing 2-campholenylidenbutanol of our invention or even less can be used to impart a rich woody and sandalwood aroma to soaps, cosmetics and other products. The amount employed will depend on considerations of cost, the nature of the end product, the effect desired in the finished product and the particular fragrance sought.

The mixture containing 2-campholenylidenbutanol of our invention as disclosed herein can be used alone, and a fragrance modifying composition or in a perfume composition as an olfactory component in detergents (anionic detergents, cationic detergents, nonionic detergents and zwitterionic detergents) and soaps; space deodorants; perfumes; colognes; bath preparations such as bath oil, bath salts; hair preparations such as lacquers, brilliantines, pomades and shampoos; cosmetic preparations such as cremes, deodorants, hand lotions, sun screens; powders such as talcs, dusting powders, face powders and the like. When the mixture containing 2-campholenylidenbutanol of our invention is used in a perfumed article such as the foregoing it can be used in amounts of from about 0.5 ppm (0.00005%) or lower. Generally, it is preferred not to use less than about 0.2% nor more than about 25% in the finished perfumed article since the use of too much will tend to unbalance the total aroma and will needlessly raise the cost of the article. Thus, the range of mixture containing 2-campholenylidenbutanol of our invention in the perfumed article is from about 0.5 ppm up to about 25% by weight of the perfumed article.

The mixture containing 2-campholenylidenbutanol of our invention can also be used in a perfumed polymer and may be imbedded into a perfumed polymer such as polyethylene, polypropylene or a polyamide such as NYLON ® by means of conventional techniques well known to those having ordinary skill in the art and by techniques such as those described in U.S. Pat. No. 4,521,541, U.S. Pat. No. 4,438,010 or U.S. Pat. No. 4,469,613 the specifications for which are incorporated by reference herein.

The following examples serve to illustrate embodiments of the invention as it is now preferred to practice it. It will be understood that these examples are illustrative and that the invention is to be restricted thereto only as indicated in the appended claims.

EXAMPLE I

PREPARATION OF MIXTURE CONTAINING 2-CAMPHOLENYLIDENBUTANOL

Reaction:

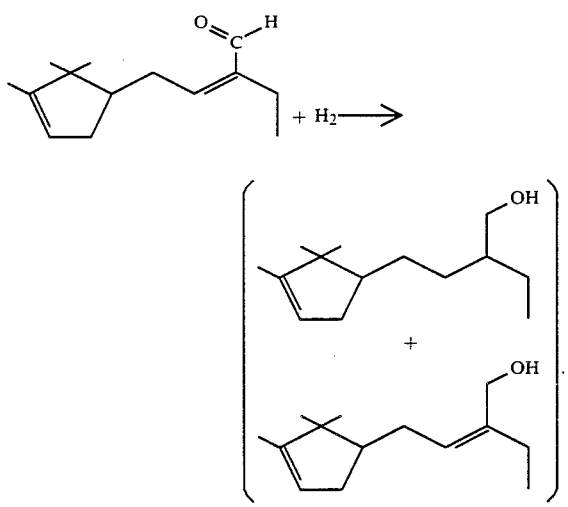

PART A: ACTIVATION OF THE CATALYST
Copper chromite catalyst (formula:

CuO.CuCr₂O₄)

Cu 0202 P manufactured by Harshaw Catalysts division of Harshaw Chemical Co., 23800 Mercantile Road, Beachwood, Ohio 44122 (7.5 grams) and methanol (200 grams) are placed in a 1 liter zipper autoclave manufactured by Autoclave Engineers Inc., of Erie, Pa. The autoclave is flushed with nitrogen three times followed by hydrogen (three times); and then charged at a pressure of 300 psig with hydrogen. The sealed autoclave is heated to 120° C. and stirred at 115°-120° C. for a period of two hours. The autoclave is then cooled and flushed with nitrogen (three times).

PART B: HYDROGENATION REACTION

To the activated catalyst in methanol is added the compound having the structure:

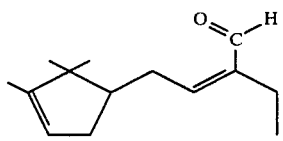

(350 grams). The autoclave was flushed with nitrogen (three times) followed by hydrogen (three times) then sealed and charged with 300 psig hydrogen and heated for a period of nine hours at 122° C. GLC analysis (conditions: 10'×0.25" 10% carbowax column programmed at 150°-225° C. at 8° C. per minute) shows an incomplete conversion. The GLC profile is set forth in FIG. 1.

Referring to FIG. 1, the peak indicated by reference numeral 10 is the peak for the aldehyde having the structure:

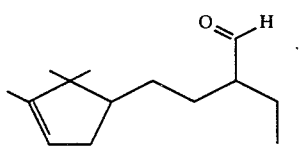

The peak indicated by reference numeral 11 is the peak for the starting material having the structure:

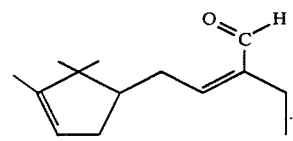

The peak indicated by reference numeral 12 is the peak for the compound having the structure:

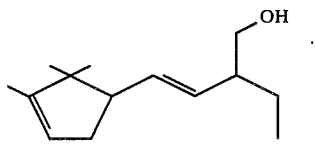

The peak indicated by reference numeral 13 is the peak for the compound having the structure:

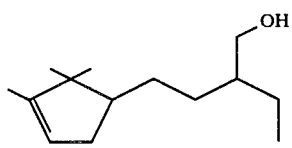

The peak indicated by reference numeral 14 is the peak for the compound having the structure:

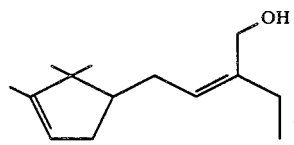

The temperature in the autoclave is then increased to 136° C. The conversion is "complete" after 30 hours at 136° C. GLC analysis shows no aldehydes present and 24% of the compound having the structure:

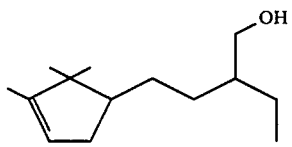

and 72% of the compound having the structure:

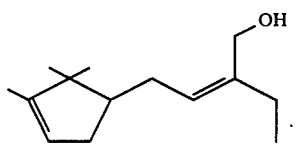

FIG. 2 is the GLC profile for the reaction product. Referring to FIG. 2, the peak indicated by reference numeral 21 is the peak for the compound having the structure:

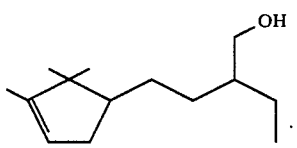

The peak indicated by reference numeral 20 is the peak for the compound having the structure:

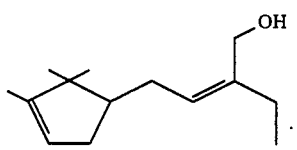

The autoclave is then cooled and flushed with nitrogen (three times) the contents were filtered over celite and distilled on a 12 plate Vigreux column from a PRIMOL ® (14 grams)—INOX ® mixture yielding the following fractions:

| FRACTION NO. | VAPOR TEMP (°C.) | LIQUID TEMP. (°C.) | VACUUM PRESSURE mm/Hg | WEIGHT OF FRACTION |
|---|---|---|---|---|
| 1-2 | 93-97 | 138 | 2.4 | 10.6 |
| 3-6 | 102 | 138 | 2.2 | 33.3 |
| 7-11 | 103 | 138 | 2.2 | 45.7 |
| 12-16 | 105 | 138-149 | 2.2 | 133.7 |
| 17-20 | 105-125 | 154-210 | 2.2-1.0 | 55.3 |

Fractions 12-16 are bulked and evaluated for odor. Bulked fractions 12-16 has an excellent highly intense woody sandalwood aroma.

FIG. 4 is the NMR spectrum for the peak indicated by reference numeral 12 on the GLC profile of FIG. 1 which is for the compound having the structure:

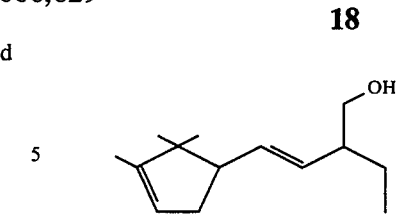

(Conditions: Field strength: 100 MHz; solvent: CFCl₃).

FIG. 5 is the infra-red spectrum for the compound of the peak indicated by reference numeral 12 in the GLC profile of FIG. 1, said compound having the structure:

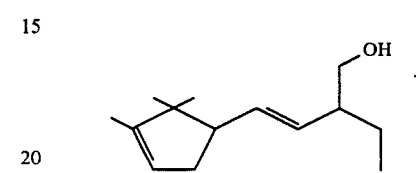

FIG. 6 is the NMR spectrum for the peak indicated by reference numeral 13 of the GLC profile of FIG. 1, for the compound having the structure:

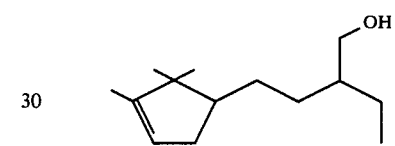

(Conditions: Field strength: 100 MHz; solvent: CFCl₃).

FIG. 7 is the infra-red spectrum for the peak indicated by reference numeral 13 of the GLC profile of FIG. 1 for the compound having the structure:

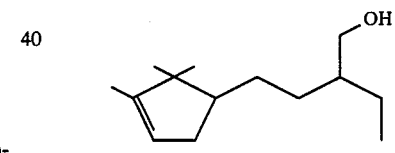

FIG. 8 is the NMR spectrum for the peak indicated by reference numeral 14 of the GLC profile of FIG. 1 for the compound having the structure:

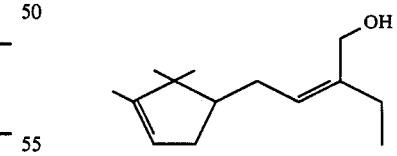

(Conditions: Field strength: 100 MHz; solvent: CFCl₃).

FIG. 9 is the infra-red spectrum for the peak indicated by reference numeral 14 of the GLC profile of FIG. 1 for the compound having the structure:

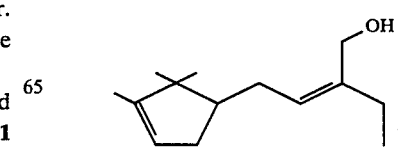

EXAMPLE II

SANDAL PERFUME FORMULATION

The following mixture is prepared:

| INGREDIENT | PARTS BY WEIGHT |
|---|---|
| 1',2',3',4',5',6',7',8'-octahydro-2',3',8',8'-tetramethyl-2'-acetonaphthone isomer mixture produced according to the process of Example VII of Application for U.S. Letters Pat. No. 434,948 filed on January 21, 1974 (now U.S. Pat. No. 3,911,018 issued on October 7, 1975) | 540 |
| Cedrenal - (A tricyclic sesquiterpinic aldehyde derived from cedrene, having the structure: ![structure] produced according to the process of U.S. Pat. Application 260,537 filed on June 7, 1972 (now U.S. Pat. No. 3,869,516 issued on March 4, 1975) (corresponding to published Dutch Appln 7,307,849 laid open for public inspection on December 11, 1973 | 90 |
| Eugenol (1% in ethyl alcohol) | 54 |
| 2,5,5-trimethyl acetyl cycloheptane produced according to Example I of U.S. Pat. Application 349,180 filed on April 9, 1973 (now U.S. Pat. No. 3,869,411 issued on March 4, 1975) | 180 |
| Borneol (1% in ethyl alcohol) | 18 |
| Hexahydro-4,7-methanonindane-2-carboxaldehyde | 18 |
| Mixture of compounds having the structures: ![struct] and ![struct] prepared according to Example I | 100 |

The mixture of compounds having the structures:

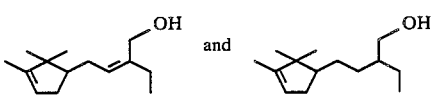

produced according to Example I (bulked fractions 13-16) imparts the woody sandalwood-like note to the instant formulation. Thus, the resulting perfume formulation can be indicated to have a sandalwood aroma with a cedarwood undertone.

EXAMPLE III

PREPARATION OF A SOAP COMPOSITION

A total of 100 grams of soap chips produced from unperfumed sodium base toilet soap made by tallow and coconut oil are mixed with 1 gram of the perfume composition produced according to Example II until its substantially homogeneous composition is obtained. The soap composition manifests a characteristic "sandal cologne" aroma having intense cedarwood nuances.

EXAMPLE IV

PREPARATION OF A SOAP COMPOSITION

A total of 100 grams of soap chips produced from unperfumed sodium base toilet soap made from tallow and coconut oil is mixed with 1 gram of the mixture of compounds having the structures:

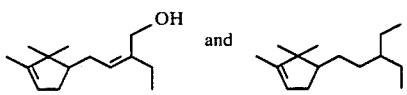

(bulked fractions 13-16) produced according to Example I until its substantially homogeneous composition is obtained. The soap composition manifests a powerful sandalwood aroma.

EXAMPLE V

PREPARATION OF A SOLID DETERGENT COMPOSITION

A total of 100 grams of a detergent powder sold under the trademark "RINSO®" are mixed with 0.15 grams of the perfume composition of Example II until a substantially homogeneous composition having a sandal cologne fragrance with cedarwood undertones is obtained.

EXAMPLE VI

PREPARATION OF COLOGNE AND HANDKERCHIEF PERFUME

The perfume composition of Example II is incorporated into a cologne having a concentration of 2.5% in 85% aqueous ethanol; and into a handkerchief perfume in a concentration of 20% (in 95% ethanol). The use of the composition of Example II affords a distinct and definite "sandal cologne" aroma having a warm sandalwood-like character and cedarwood undertones to the handkerchief perfume and to the cologne.

EXAMPLE VII

PREPARATION OF COLOGNE AND HANDKERCHIEF PERFUME

The mixture of compounds having the structures:

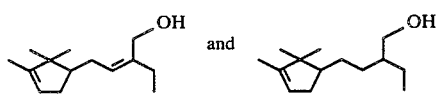

(bulked fractions 13-16) produced according to Example I is incorporated into colognes having concentrations of 2.0%, 2.5%, 3.0%, 3.5%, 4.0%, 4.5% and 5.0% in 85% aqueous food grade ethanol and into handkerchief perfumes in concentrations of 15%, 20%, 25%, 30% and 35% (in 95% food grade ethanol). The uses of the mixture of compounds having the structures:

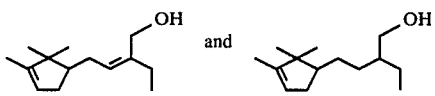

produced according to Example I (bulked fractions 13–16) affords a distinct and definitive sandalwood aroma to the handkerchief perfumes and to the colognes prepared as above.

EXAMPLE VIII

PERFUMED LIQUID DETERGENT

Concentrated liquid detergents with a strong sandalwood aroma are prepared containing 0.10%, 0.15% and 0.20% of a mixture of compounds containing compounds having the structures:

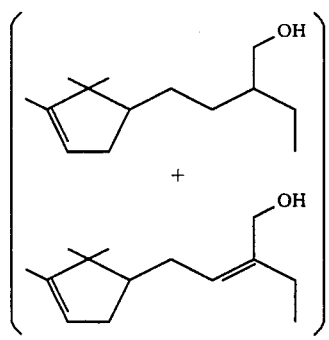

prepared according to Example I, bulked fractions 12–16. The liquid detergents are prepared by adding and homogeneously mixing the appropriate quantity of said mixture of compounds in the liquid detergent described according to United Kingdom Specification No. 1,092,149 (the specification for which is incorporated by reference herein) containing 2% by weight ethyl/maleic anhydride copolymer (specific viscosity 0.5–1.0) and 0.42 weight percent methyl vinyl ethyl/maleic anhydride copolymer (specific viscosity 0.4) as stabilzer and 8% by weight of a sultaine detergent. The detergents all possess strong sandalwood aromas with sweet nuances, the intensity increasing with greater concentration of compound prepared according to Example I.

EXAMPLE IX

PREPARATION OF DETERGENT COMPOSITION

A total of 100 grams of a detergent powder (essentially water soluble non-ionic detergent and stable laundry enzyme as described in U.S. Pat. No. 3,953,353 issued on Apr. 27, 1976, the specification for which is incorporated by reference herein) is mixed with 0.15 grams of the perfume composition of Example II until a substantially homogeneous composition is obtained. The composition has an excellent sandalwood aroma with cedarwood undertones.

What is claimed is:

1. A mixture of compounds comprising as a major quantity the compounds having the structures:

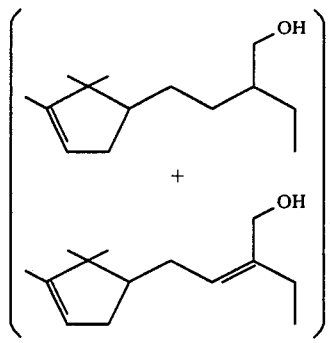

produced according to the process consisting essentially of the steps of:

(i) reacting the aldehyde having the structure:

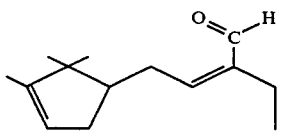

with hydrogen over a copper chromite catalyst having the formula:

$CuO.CuCr_2O_4$ in the absence of additional reagents and in the absence of additional base, according to the reaction:

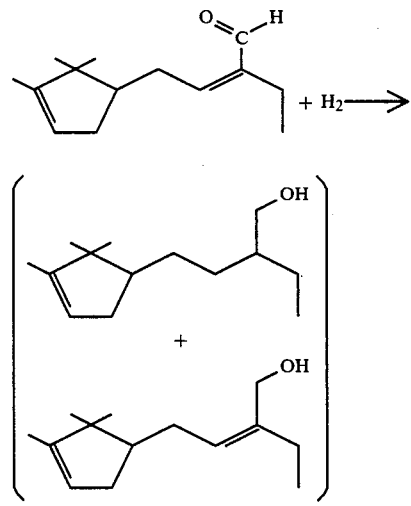

at a temperature in the range of from about 110° C. up to about 220° C.; at a pressure in the range of from about 100 up to about 1000 psig; the weight percent of catalyst based on reactant having the structure:

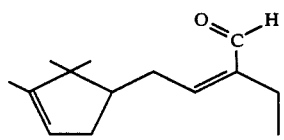

being from about 1 weight percent up to about 6 weight percent; the time of reaction being such that the reaction is terminated when 70-80% of the compound having the structure:

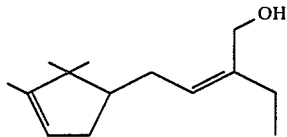

is in the reaction mass and the remainder of the reaction mass is primarily the compound having the structure:

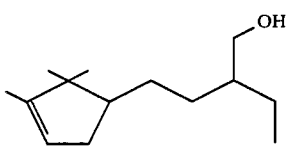

and then (ii) recovering the resulting mixture by fractional distillation.

2. A mixture of compounds comprising as a major quantity the compounds having the structures:

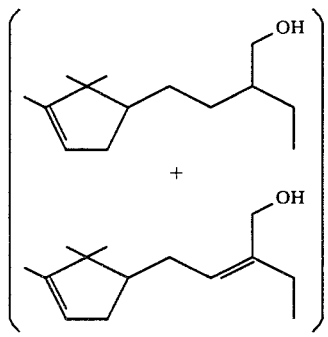

produced according to the process consisting essentially of the steps of:

(i) reacting the aldehyde having the structure:

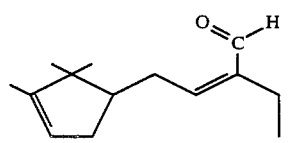

over a catalyst consisting essentially of copper chromite having the formula:

and a minor proportion of barium oxide in the absence of additional reagents and in the absence of additional base, according to the reaction:

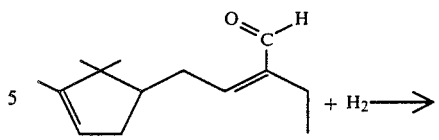

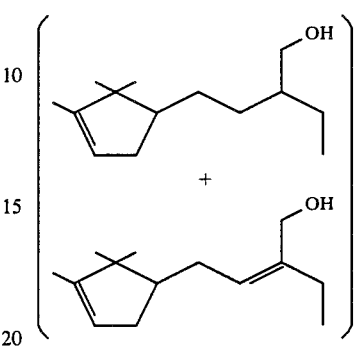

at a temperature in the range of from about 110° C. up to about 220° C.; at a pressure in the range of from about 100 up to about 1000 psig; the weight percent of catalyst based on reactant having the structure:

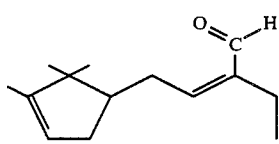

being from about 1 weight percent up to about 6 weight percent; the time of reaction being such that the reaction is terminated when 70-80% of the compound having the structure:

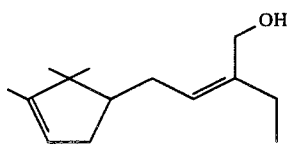

is in the reaction mass and the remainder of the reaction mass is primarily the compound having the structure:

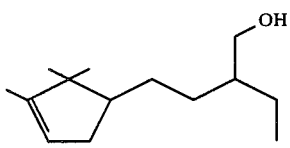

and then (ii) recovering the resulting mixture by fractional distillation.

3. The process for augmenting or enhancing the aroma of a consumable material selected from the group consisting of perfume compositions, colognes and perfumed articles comprising the step of adding to said consumable material, an aroma augmenting or enhancing quantity of the product defined according to either of claims 1 or 2.

4. The process of claim 3 wherein the consumable material is a perfume composition or cologne.

5. The process of claim 3 wherein the consumable material is a perfumed article and the perfumed article is a solid or liquid anionic, cationic, nonionic or zwitterionic detergent.

* * * * *